(12) United States Patent
Touzan et al.

(10) Patent No.: US 6,210,656 B1
(45) Date of Patent: *Apr. 3, 2001

(54) SELF-FOAMING CREAM

(75) Inventors: Philippe Touzan, Paris; Patricia Delambre, Ablon-sur-Seine, both of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/292,372

(22) Filed: Apr. 15, 1999

Related U.S. Application Data

(63) Continuation of application No. 08/949,684, filed on Oct. 14, 1997, now Pat. No. 6,033,647.

(30) Foreign Application Priority Data

Oct. 14, 1996 (FR) .................................................. 96 12510

(51) Int. Cl.$^7$ ....................................................... A61K 7/48
(52) U.S. Cl. .................... 424/45; 424/401; 424/70.11; 424/70.22; 424/70.27; 514/938
(58) Field of Search .................................. 424/401, 70.1, 424/70.11, 70.122, 70.15, 70.16, 70.22, 70.27, 45, DIG. 1; 514/938

(56) References Cited

U.S. PATENT DOCUMENTS

| | | | |
|---|---|---|---|
| 4,237,243 | * 12/1980 | Quack et al. | 525/154 |
| 5,078,990 | * 1/1992 | Martin et al. | 424/70 |
| 5,603,926 | * 2/1997 | Matsumoto et al. | 424/70.15 |
| 5,637,291 | * 6/1997 | Bara et al. | 424/59 |
| 5,690,946 | * 11/1997 | Koulbanis et al. | 424/401 |
| 5,776,444 | * 7/1998 | Birtwistle et al. | 424/70.12 |

* cited by examiner

Primary Examiner—Thurman K. Page
Assistant Examiner—Lakshmi Channavajjala
(74) Attorney, Agent, or Firm—Oblon, Spivak, McClelland, Maier & Neustadt, P.C.

(57) ABSTRACT

A self-foaming composition in the form of a post-foaming, pressurizable oil-in-water emulsion comprising:

(A) at least 5% by weight, relative to the total weight of the composition, of a fatty phase comprising at least one cosmetic oil, (B) a gelling system comprising at least one emulsifying polymer which is selected from the group consisting of:

(1) crosslinked homopolymers formed from at least one cationic or anionic monomer containing ethylenic unsaturation selected from the group consisting of ammonium (meth)acrylate; 2-acrylamido-2-methylpropanesulfonic acid as well as its salts, dialkylaminoalkyl (meth)acrylates, dialkylaminoalkyl (meth) acrylamide and its quaternary salts or acids, wherein the crosslinking agent which forms the crosslinking contains ethylenic polyunsaturation, and (2) crosslinked copolymers formed from at least one cationic or anionic monomer containing ethylenic unsaturation, from at least one nonionic comonomer and from a crosslinking agent containing ethylenic polyunsaturation; and (C) water.

26 Claims, No Drawings

SELF-FOAMING CREAM

This application is a Continuation of application Ser. No. 08/949,684 Filed on Oct. 14, 1997, U.S. Pat. No. 6,033,647.

BACKGROUND OF THE INVENTION

1. Field of the Invention

The present invention relates to self-foaming creams in the form of a pressurizable oil-in-water emulsion, as well as to post-foaming pressurized devices containing them. These creams for topical use have good foaming power and are intended more particularly to cleanse and care for the skin.

2. Description of the Background

Cleansing the skin is very important for facial care. It must be as efficient as possible, since greasy residues such as excess sebum, the residues of the cosmetic products used daily and make-up products, in particular waterproof products, accumulate in the folds and at the surface of the skin and may obstruct the pores, leading to the development of spots. Among other causal factors, poor quality cleansing is often responsible for a muddy complexion.

Several major types of skin cleansing products are known such as foaming detergent aqueous gels and lotions and rinsable cleansing anhydrous gels and oils, cleansing milks and foaming creams, which are usually soap-based.

Foaming detergent aqueous gels and lotions have a cleansing action imparted by surfactants which place the fatty residues and the pigments of the makeup products in suspension. They are cosmetically pleasant and efficient because they foam and they are easily removed. Since they contain no cosmetic oil, they have the drawback of drying the skin by their delipidating action. This is the case, for example, of the products described in WO 95/05769, which teaches very fluid, pressurizable skin cleansing lotions which produce a beautiful mousse, but these products destroy the skin's hydrolipid film and leave the skin clean but rough.

Rinsable anhydrous gels and oils have a cleansing action by means of the oils contained in these formulations. These oils make it possible to dissolve greasy residues and to disperse make-up pigments. These products are efficient and well-tolerated. They have the drawback of being heavy, of not foaming and of not giving a sensation of freshness when applied, which is detrimental in cosmetic terms.

Cleansing milks and creams contain both detergent surfactants, emulsifiers and oils in sufficiently low amounts so as not to destabilize the emulsion. Despite their good efficacy, these products are non-foaming and are of insufficient rinsability, thus making it necessary to use an additional detergent tonic lotion in order to improve the rinsing and the removal of soiling. Besides its astringent nature, the use of this second product may lead to long-term drying of the skin.

An existing objective has been to design cleansing foaming products that are fully rinsable with water, containing few or no surfactants and able to comprise oils in large amounts if so desired, in order to optimize the cleansing of the skin and to moisturize and nourish it by avoiding any drying or irritation of the skin. A desired objective is a cream which has the efficacy of a soap cream (cleansing power and foaming), but not its drawbacks, in particular the stripping of the skin which is associated with a large percentage of foaming surfactants.

In order to produce such a product, it is not possible simply to introduce oils into an aqueous gel or lotion, since oils tend to inhibit the foaming properties of these formulations, that is, the oils are said to "kill" the foam. Furthermore, the dispersion of the oil is unstable. Foaming emulsions, for example cleansing emulsions, are known as shown in WO 95/17163. This type of product is very mild and very well-tolerated by the skin, but the foaming power of these emulsions is low because of the presence of oils. In addition, these emulsions are relatively thick, which does not allow them to be packaged in pressurized containers.

Moreover, it is known, for example, as taught in WO 89/11907, that the phase inversion method makes it possible to prepare stable, fluid oil-in-water emulsions. However, the emulsions prepared by the phase inversion method in the prior art are non-foaming and are delivered in the form of spray when they are pressurized. In addition, they comprise appreciable amounts of surfactants.

Creams in the form of foaming, pressurized oil-in-water emulsions, comprising at least 2% of a nonionic surfactant, up to 21% of oil and from 0.5–4.5% of a consistency agent, are known as described in U.S. Pat. No. 4,808,388. Such compositions are only delivered in a satisfactory manner (sheen, firmness, density) if $CO_2$ or $N_2O$ is used as the propellant gas. A need continues to exist for an improved self foaming skin or hair treating composition.

SUMMARY OF THE INVENTION

Accordingly, one object of the present invention is to provide a hair and skin treating composition which is more tolerant than those of the prior art, in the form of pressurizable, self-foaming creams comprising less than 2% of in surfactants, preferably no surfactants at all.

Briefly this object and other objects of the present invention as hereinafter will become more readily apparent can be attained by a self-foaming composition in the form of a post-foaming, pressurizable oil-in-water emulsion comprising:

(A) at least 5% by weight, relative to the total weight of the composition, of a fatty phase comprising at least one cosmetic oil, (B) a gelling system comprising at least one emulsifying polymer which is selected from the group consisting of:

(1) crosslinked homopolymers formed from at least one cationic or anionic monomer containing ethylenic unsaturation selected from the group consisting of ammonium (meth)acrylate; 2-acrylamido-2-methylpropanesulfonic acid as well as its salts, dialkylaminoalkyl (meth)acrylates, dialkylaminoalkyl (meth)acrylamide and its quaternary salts or acids, wherein crosslinking agent which forms the crosslinking contains ethylenic polyunsaturation, and (2) crosslinked copolymers formed from at least one cationic or anionic monomer containing ethylenic unsaturation, from at least one nonionic comonomer and from a crosslinking agent containing ethylenic polyunsaturation; and (C) water.

DETAILED DESCRIPTION OF THE PREFERRED EMBODIMENTS

The term "self-foaming" is understood to refer to a composition which is able to give rise to of a foam and which contains less than 2% of surfactants. The term "post-foaming" is understood to refer to a composition which, when pressurized, is delivered in the form of a cream, this cream foaming spontaneously when it is spread or worked onto the skin by hand.

The emulsions of the invention may be pressurized and packaged in aerosol containers.

An aspect of the invention is also an aerosol device consisting of a pressurizable container fitted with a diffusion means comprising a valve, the said container comprising a propulsion means such as, for example, a propellant gas and a composition of the invention.

When a pressure is exerted on the diffusion means, the valve is actuated and the device delivers its contents in the form of a smooth cream. When applied on the skin, this cream transforms into a dense, fine, smooth, abundant and firm mousse. Products of such a consistency are particularly valued for skin or hair cleansing and care.

The post-foaming compositions are entirely different from standard, pressurized foaming compositions which are distributed in the form of a mousse, as is the case, for example, of the compositions described in U.S. Pat. No. 4,808,388.

The crosslinked copolymers used in the compositions of the invention comprise at least one cationic or anionic monomer containing ethylenic unsaturation, at least one nonionic comonomer and a crosslinking agent containing ethylenic polyunsaturation. The anionic monomer is selected in particular from (meth)acrylic acid, ammonium (meth)acrylate and 2-acrylamido-2-methylpropanesulphonic acid, as well as its salts.

The cationic monomer is selected in particular from dialkylaminoalkyl (meth)acrylates, preferably dimethylaminoethyl methacrylate; dialkylaminoalkyl(meth)acrylamides and their quaternary salts or acids; the alkyl radicals preferably containing one to four carbon atoms.

The nonionic comonomer preferably is selected from methacrylamide, acrylamide, $C_{10}$–$C_{30}$ (meth)acrylic acid esters and vinyl esters.

The crosslinking agents containing ethylenic polyunsaturation are preferably selected from divinylbenzene; tetraallyloxyethane; diallyl ether; polyallyl polyglyceryl ethers; allylic ethers of alcohols of the sugar series such as erythritol, pentaerythritol, arabitol, sorbitol and glucose; methylenebisacrylamide, ethylene glycol di(methyl) acrylate, di(meth)acrylamide, cyanomethyl acrylate and vinyloxyethyl (meth)acrylate or their metal salts.

The emulsifying polymers used in the compositions of the invention are preferably selected from the group of:

(a) copolymers containing a major fraction of acrylic acid and a minor fraction of $C_{10}$–$C_{30}$ (meth)acrylic acid esters, such as the products sold under the names Pemulen TRY, Pemulen TR2 and Carbopol 1342 by the company Goodrich (they are prepared as described in EP 0 268 164);

(b) copolymers of 2-acrylamido-2-methylpropanesulphonic acid, which is partially or totally neutralized with a base such as sodium hydroxide, potassium hydroxide or an amine, and of acrylamide, such as the products described in Example 1 of document EP 0 503 853;

(c) homopolymers of dimethylaminoethyl methacrylate quaternized with methyl chloride such as the products sold under the names Salcare 95 and Salcare 96 by the company Allied Colloids or copolymers of dimethylaminoethyl methacrylate, quaternized with methyl chloride, and of acrylamide, such as the product Salcare SC92 sold by Allied Colloids or the product PAS 5194 sold by Hoechst (They are prepared as described in EP 0 395 282).

(d) Copolymers of (meth)acrylic acid and of vinyl esters such as copolymers of acrylic acid and vinyl isodecanoate, for example the products sold under the names STABYLEN 30 and PNC 300 by the company 3V.

The crosslinked homopolymers or copolymers employed in the composition of the invention are selected more particularly from those defined in paragraphs (a) and (b) above.

Preferably, the gelling system (B) also contains at least one natural or synthetic hydrophilic gelling agent which may be selected from natural or modified gums and from hydrophilic synthetic polymers having gelling properties.

The expression natural or modified gum is understood to refer to an optionally modified polysaccharide which becomes hydrated in an aqueous medium in order to form a viscous solution or a dispersion. Among natural gums which are included are algal extracts, plant exudates and gums extracted from plant seeds or roots and those obtained by microbiological fermentation. The modified or semi-synthetic gums comprise cellulose derivatives and starch derivatives and, in general, the derivatives of all natural gums.

All the compounds cited in the following documents are included in the definition of gums of the present invention:

"Gums, Encyclopedia of Chemical Technology, Kirk-Othmer", Vol. 12, pp. 842–862, 4th edition, 1994, Wiley.

"Starch, Encyclopedia of Chemical Technology, Kirk-Othmer", Vol. 21, pp. 492–507, 3rd edition, 1985, Wiley.

"Cellulose esters, Encyclopedia of Chemical Technology, Kirk-Othmer", Vol. 5, pp. 496–540, 4th edition, 1993, Wiley.

"Cellulose ethers, Encyclopedia of Chemical Technology, Kirk-Othmer", Vol. 5, pp. 541–563, 4th edition, 1993, Wiley.

The gums used in the compositions of the present invention are preferably chosen from polyholosides, such as carrageenans or xanthan gum, and their derivatives.

Suitable synthetic polymers having gelling properties are defined and disclosed in:

"Resins, water soluble. Encyclopedia of Chemical Technology, Kirth-Othmer", Vol. 20, pp. 207–230, 3rd edition, 1978, Wiley.

Synthetic polymers having gelling properties, which may be used in the present invention include, in particular, carboxyvinyl polymers (carbomer) such as the products sold under the names Carbopol 980, 981, 954, 2984 and 5984 by the company Goodrich or the products sold under the names Synthalen M and Synthalen K by the company 3 VSA;

Preferably, the emulsions which are the subject of the invention comprise from 0.1–2% of a gelling system (B), this preferably comprising at least 0.05%, relative to the final composition, of at least one emulsifying polymer.

The compositions of the invention may also comprise one or several surfactants in an amount less than 2% by weight, preferably in an amount less than 1.5% by weight. In this case, the surfactant may be selected from any known class of surfactants. Suitable surfactants are, in fact, disclosed in "Encyclopedia of Chemical Technology, Kirk-Othmer", Vol. 22, pp. 333–432, 3rd edition, 1979, Wiley, which surfactants are the main classes of surfactants known to those skilled in the art, along with their functions (in particular whether or not they form a foam). Advantageously, when a surfactant is introduced into the compositions of the invention, a foaming surfactant is selected. Although a very satisfactory mousse is obtained in the absence of surfactant, the presence of a foaming surfactant may promote the formation of a more aerated and voluminous mousse.

The foaming surfactants of the present invention are selected from surfactants having a foaming power characterized by a foam height of more than 100 mm, preferably of more than 120 mm, measured according to the Ross-Miles method for a 0.1% by weight solution of surfactant in distilled water at 25° C. They may be present in a proportion of 0–2% by weight, preferably 0.5–1.5% by weight, relative to the final composition.

The nature of the fatty phase forming part of the composition of the emulsions of the invention is not critical, and it may thus be made up of all the compounds which are already generally known as being suitable for the manufacture of oil-in-water emulsions. In particular, these compounds may be selected, alone or as mixtures, from various fatty substances, oils of plant, animal or mineral origin, natural or synthetic waxes, and the like.

Oils which may be used in the present invention include oils of plant or animal origin such as, for example, perhydrosqualene, squalane, coconut oil, macadamia oil, mink oil, turtle oil, soybean oil, grapeseed oil, sesame oil, corn oil, rapeseed oil, sunflower oil, cottonseed oil, avocado oil, olive oil, castor oil, jojoba oil and groundnut oil; hydrocarbon oils such as liquid paraffin and petroleum jelly; silicone oils such as polymethylsiloxanes, polymethylphenylsiloxanes, polysiloxanes modified with fatty acids, polysiloxanes modified with fatty alcohols, polysiloxanes modified with polyoxyalkylenes, and fluorosilicones; perfluoro and/or organofluoro oils; higher fatty acids such as myristic acid, palmitic acid, stearic acid, behenic acid, oleic acid, linoleic acid, linolenic acid and isostearic acid, higher fatty alcohols such as cetanol, stearyl alcohol and oleyl alcohol; mono- and diesters include, in particular, isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, 2-diethylhexyl succinate, diisostearyl malate, 2-octyldodecyl lactate, glyceryl triisostearate, di-n-butyl adipate, bis(2-ethylhexyl)adipate, ethylene glycol dioleate, ethylene glycol diisotridecanoate, ethylene glycol diisostearate and neopentyl glycol dicaprylate.

Obviously, the fatty phase may also contain one or more standard lipophilic cosmetic adjuvants.

The fatty phase represents at least 5% of the total weight of the final composition and may up to 50% by weight of the total weight of the composition without the foaming power of these compositions being endangered. The fatty phase preferably represents from 5–40%, and more preferably from 10–30% of the total weight of the composition.

The fatty phase may consist solely of cosmetic oil, the weight proportion of which relative to the total weight of the composition may reach 50%; it may also comprise animal, plant or synthetic waxes, preferably in amounts less than 1%.

Preferably, the compositions of the invention comprise from 5–40% by weight, relative to the total weight of the composition, of at least one cosmetic oil, and even more preferably from 10–30%. The emulsions of the invention comprise water. Usually, water is understood to refer to demineralized water. However, part of the water used in the emulsions according to the invention may optionally be chosen from mineral water or spring water. In general, a mineral water is fit for consumption, which is not always the case of a spring water. Each of these waters contains, inter alia, dissolved minerals and trace elements. These waters are known to be used for specific treatment purposes depending on the particular trace elements and minerals which they contain, such as moisturization and desensitization of the skin or the treatment of certain dermatoses. The terms mineral water and spring water will be understood to denote not only natural mineral or spring waters but also natural mineral or spring waters enriched with additional mineral and/or trace-element constituents, as well as mineral and/or trace-element aqueous solutions prepared from purified (demineralized or distilled) water.

A natural spring or mineral water used according to the invention may be chosen, for example, from Eau de Vittel, the waters from the Vichy basin, Eau d'Uriage, Eau de la Roche Posay, Eau de la Bourboule, Eau d'Enghien-les-Bains, Eau de Saint Gervais-les-Bains, Eau de Neris-les-Bains, Eau d'Allevar-les-Bains, Eau de Digne, Eau de Maizieres, Eau de Neyrac-les-Bains, Eau de Lons-le-Saunier, les Eaux Bonnes, Eau de Rochefort, Eau de Saint Christau, Eau des Fumades and Eau de Tercis-les-bains.

In a conventional manner, the dispersing aqueous phase may consist of water or of a mixture of water and polyhydric alcohol(s) such as, for example, glycerol, propylene glycol and sorbitol, or alternatively a mixture of water and water-soluble lower alcohol(s) such as ethanol, isopropanol or butanol (aqueous-alcoholic solution), and they may, obviously, also contain standard water-soluble cosmetic adjuvants.

The cosmetic or dermatological emulsions of the invention may also contain from 0.01–10% by weight, relative to the total weight of the composition, of at least one cosmetically acceptable water-soluble or liposoluble adjuvant such as preserving agents, antioxidants, fragrances, screening agents, dyestuffs, and hydrophilic or lipophilic active agents.

The active agents for the skin may be anti-ageing active agents, anti-wrinkle active agents, moisturizers, wetting agents, slimming active agents, depigmenting active agents, anti-free-radical (oxygen radical species) agents, nourishing active agents, protective active agents, restructuring active agents, firming active agents, anti-acne active agents, exfoliant active agents, emollient active agents or alternatively active agents for treating skin diseases such as mycosis, dermatitis, psoriasis, etc. These active agents are used, depending on their nature, in the usual proportions for emulsions and, for example, from 0.01–10% by weight relative to the total weight of the composition.

Usually, a pressurized device within the scope of the invention contains 0.5–20% of propellant gas and 80–99.5% of emulsion. Any propellant gas known for such applications may be used in the present devices including, in particular, hydrocarbon gases such as propane, isopropane, n-butane, isobutane, isopentane and mixtures thereof; fluoro gases such as chlorodifluoromethane, dichlorodifluoromethane, difluoroethane, chlorodifluoroethane, dichlorotetrafluoroethane, and the like, and mixtures thereof. Nitrogen and carbon dioxide and mixtures thereof may also be used as propellant gases in the present invention.

Preferably, a gas having a boiling point not greater than 30° C. is selected, such gases promoting the post-foaming phenomenon. Preferably, these gases are selected from hydrocarbons, in particular isopentane, isobutane and mixtures thereof.

Another aspect of the invention is the use of the present composition as a cosmetic composition for application to the skin and/or the hair, in particular to treat and/or to cleanse and/or to care for the skin.

An aspect of the present invention is also the use of the composition for the manufacture of a dermatological compositions in order to treat and/or to cleanse and/or to care for the skin and/or the hair.

The present composition comprises little or no surfactant and is particularly suitable to care for and/or treat and/or cleanse sensitive skins.

A cosmetic treatment process for the skin or the hair consists in applying an effective amount of a cosmetic composition as defined above to the skin or the hair.

Having generally described this invention, a further understanding can be obtained by reference to certain specific examples which are provided herein for purposes of illustration only and are not intended to be limiting unless otherwise specified.

The amounts of components in the examples are given as weight of active material relative to the total weight of the composition.

The names of the starting materials are the CTFA names.

EXAMPLE 1

| self-foaming cleansing cream | |
|---|---|
| Mineral oil | 15% |
| $C_{13}$—$C_{14}$ isoparaffin | 0.6% |
| Glycerol | 6% |
| Sodium laureth sulfate | 1% |
| Laureth-7 | 0.2% |
| Polyacrylamide (*) | 1.2% |
| Carbomer | 0.1% |
| Sodium hydroxide | 0.04% |
| Fragrance | qs |
| Preserving agents | qs |
| Water | qsp 100 |

(*) marketed under the name Sepigel by the company Seppic.

Procedure:

The polymers (Carbomer, acrylic polymer and gums) are swollen in hot (60° C.) water with stirring. The propylene glycol is introduced, followed by sodium hydroxide. After neutralization with sodium hydroxide, the preserving agents are introduced. The oil and the fragrance are dispersed with stirring (turbomixer) in order to obtain a smooth and shiny emulsion.

The emulsion is introduced into a pressurized aerosol container with 3.5% of isopentane.

By actuating the valve of the device, it delivers its contents in the form of a cream which transforms into a mousse on contact with the skin.

EXAMPLE 2

| self-foaming cleansing cream for sensitive skins | |
|---|---|
| Octyl palmitate | 10% |
| Propylene glycol | 5% |
| Carbomer | 0.3% |
| Acrylate/$C_{10}$—$C_{30}$ alkylacrylate crosspolymer (*) | 0.2% |
| Xanthan gum | |
| Sodium hydroxide | 0.3% |
| Fragrance | 0.18% |
| Preserving agents | qs |
| Water | qsp |

(*) marketed under the brand name Pemulen by the company Goodrich.

An emulsion is prepared in accordance with the above example, and this emulsion is then introduced into a pressurized aerosol container with 3.5% of isopentane.

By actuating the valve of the device, it delivers its contents in the form of a cream which transforms into a fine, dense, smooth mousse by massaging it on the skin.

EXAMPLE 3

| self-foaming cleansing cream | |
|---|---|
| Octyl palmitate | 10% |
| Mineral oil | 10% |
| Sodium laureth sulfate | 1.5% |
| Propylene glycol | 3% |
| Carbomer | 0.6% |
| Acrylate/$C_{10}$—$C_{30}$ alkylacrylate crosspolymer (*) | 0.2% |
| Sodium hydroxide | 0.35% |
| Fragrance | qs |
| Preserving agents | qs |
| Water | qsp 100 |

(*) marketed under the brand name Pemulen by the company Goodrich.

An emulsion is prepared in accordance with Example 1, and this emulsion is then introduced into a pressurized aerosol container with 3.5% of isopentane.

By actuating the valve of the device, it delivers its contents in the form of a cream which transforms into a fine, dense, smooth mousse upon massaging into the skin.

The disclosure of French priority application 96-12510 filed Oct. 14, 1996 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is desired to be secured by Letters Patent of the United States is:

1. A self-foaming composition in the form of a post-foaming, pressurizable oil-in-water emulsion consisting essentially of:
   (A) at least 5% by weight, relative to the total weight of the composition, of a fatty phase comprising at least one cosmetic oil,
   (B) a gelling system comprising at least one emulsifying polymer;
   wherein said emulsifying polymer is selected from the group consisting of:
   (a) a copolymer containing a major fraction of acrylic acid and a minor fraction of a $C_{10}$–$C_{30}$ (meth)acrylic acid ester;
   (b) a copolymer of partially or totally neutralized 2-acrylamide-2-methylpropanesulfonic acid and of acrylamide;
   (c) a homopolymer of dimethylaminoethyl methacrylate quaternized with methyl chloride or a copolymer of said dimethylaminoethyl methacrylate quaternized with methyl chloride with acrylamide; and
   (d) a copolymer of (meth)acrylic acid and of a vinyl ester;
   (C) water; and
   (D) from 0 to a total of less than 2% by weight of at least one surfactant.

2. The composition of claim 1, which comprises 0–1.5% by weight of at least one surfactant.

3. The composition of claim 1, wherein the anionic monomer is selected from the group consisting of (meth) acrylic acid, ammonium (meth)acrylate and 2-acrylamido-2-methylpropanesulfonic acid, and salts thereof.

4. The composition of claim 1, wherein the cationic monomer is selected from the group consisting of dialkylaminoalkyl (meth)acrylates, and dialkylaminoalkyl (meth) acrylamides and its quaternary salts or acid.

5. The composition of claim 1, wherein the nonionic comonomer is selected from the group consisting of methacrylamide, acrylamide, $C_{10}$–$C_{30}$ (meth)acrylic acid esters and vinyl, esters.

6. The composition of claim 1, wherein the crosslinking agents containing ethylenic polyunsaturation are selected from the group consisting of divinylbenzene, tetraallyloxyethane, diallyl ether, polyallyl polyglyceryl ethers, allylic ethers of sugar alcohols, methylenebisacrylamide, ethylene glycol di(methyl)acrylate, di(meth)acrylamide, cyanomethyl acrylate and vinyloxyethyl (meth)acrylate and metal salts thereof.

7. The composition of claim 1, wherein the gelling system (B) also contains at least one natural or synthetic hydrophilic gelling agent.

8. The composition of claim 7, wherein the hydrophilic gelling agent is selected from the group consisting of natural or modified gums and hydrophilic synthetic polymers.

9. The composition of claim 8, wherein the hydrophilic gelling agent is selected from the group consisting of xanthan gum, carrageenans and their derivatives, and carboxyvinylpolymers.

10. The composition of claim 1, which contains from 0.1–2% of a gelling system (B).

11. The composition of claim 1, wherein the gelling system (B) comprises at least 0.05% by weight, relative to the final composition, of at least one emulsifying polymer.

12. The composition of claim 1, which comprises at least a foaming surfactant.

13. The composition of claim 12, wherein the foaming surfactant has a foaming power determined by a foam height of more than 100 mm, measured according to the Ross-Miles method for a 0.1% by weight solution of surfactant in distilled water at 25° C.

14. The composition of claim 1, which comprises up to 50% by weight of fatty phase relative to the total weight of the composition.

15. The composition of claim 1, which comprises up to 50% by weight of at least one cosmetic oil relative to the total weight of the composition.

16. The composition of claim 1, which comprises 5–40% by weight, relative to the total weight of the composition, of at least one cosmetic oil.

17. The composition of claim 1, which comprises at least one mineral water or spring water.

18. The composition of claim 17, wherein the spring or mineral water is selected from the group consisting of Eau de Vittel, the waters from the Vichy basin, Eau d'Uriage, Eau de la Roche Posay, Eau de la Bourboule, Eau d'Enghien-les-Bains, Eau de Saint Gervais-les-Bains, Eau de Neris-les-Bains, Eau d'Allevar-les-Bains, Eau de Digne, Eau de Maizieres, Eau de Neyrac-les-Bains, Eau de Lons-le-Saunier, les Eaux Bonnes, Eau de Rochefort, Eau de Saint Christau, Eau des Fumades and Eau de Tercis-les-bains.

19. The composition of claim 1, which comprises from 0.01–10% by weight, relative to the total weight of the composition, of at least one cosmetic water-soluble or liposoluble adjuvant selected from the group consisting of preserving agents, antioxidants, fragrances, screening agents, dyestuffs, and hydrophilic or lipophilic active agents.

20. An aerosol device consisting of a pressurizable container fitted with a diffusion means comprising a valve, the said container comprising a propulsion means and a composition of claim 1.

21. The device of claim 20, which contains 0.5–20% of propellant gas as propulsion means and 80–99.5% of composition.

22. The device of claim 20, which propulsion means is isopentane, isobutane or mixtures thereof.

23. A method of treating the skin and/or hair, comprising:
applying the composition of claim 1 to the skin and or the hair.

24. The method of claim 23, wherein the skin is treated, cleansed or cared for.

25. The method of claim 23, wherein sensitive skin is treated, cleansed or cared for.

26. A method of manufacturing a dermatological composition for the treatment, cleansing or care of the skin and/or hair, comprising:
combining the composition of claim 1 with other dermatological components.

* * * * *